US005908611A

United States Patent [19]

Gottlieb et al.

[11] Patent Number: 5,908,611

[45] Date of Patent: *Jun. 1, 1999

[54] TREATMENT OF VISCOUS MUCOUS-ASSOCIATED DISEASES

[75] Inventors: Roberta A. Gottlieb; Bernard M. Babior, both of San Diego, Calif.

[73] Assignee: The Scripps Research Institute, La Jolla, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/435,147

[22] Filed: May 5, 1995

[51] Int. Cl.[6] .................................................. A61K 9/12

[52] U.S. Cl. ............................ 424/45; 424/46; 514/958; 514/851

[58] Field of Search ....................... 424/45, 46; 514/958, 514/851

[56] References Cited

U.S. PATENT DOCUMENTS

| | | | |
|---|---|---|---|
| 5,292,498 | 3/1994 | Boucher et al. | 424/45 |
| 5,512,269 | 4/1996 | Molina y Vedia et al. | 424/45 |
| 5,635,160 | 6/1997 | Stutts, III et al. | 424/45 |

OTHER PUBLICATIONS

Barash et al., "Defective Acidication of Intracellular Organelles in Cystic Fibrosis", Nature, 352:70–73.

Barry et al., "Endonuclease Activation During Apoptosis: The Role of Cytosolic Ca2+ and pH", Biochem. Biophys. Res. Commun., 186:782–789 (1992).

Barry et al., "Etoposide–Induced Apoptosis in Human HL–60 Cells is Associated with Intracellular Acidification", Cancer Res., 53:2349–2357 (1993).

Caceres–Cortes et al., "Product of the Steel Locus Suppresses Apoptosis in Hemopoietic Cells," J. Biol. Chem., 269:12084–12091 (1994).

Elgavish et al., "Altered Sulfate Transport via Anion Exchange in CFPAC is Corrected by Retrovirus–Mediated CFTR Gene Transfer", Am. J. Physiol., 263:C176–186 (1992).

Karuri et al., "Selective Cellular Acidification and Toxicity of Weak Organic Acids in an Acidic Micro environment", Brit. J. Cancer, 68:1080–1087 (1993).

Keal, "Biochemistry and Rheology of Sputum in Asthma", Postgrad. Med. J., 47:171–177 (1971).

Knowles et al., "A Pilot Study of Aerosolized Amiloride for the Treatment of Lung Disease in Cystic Fibrosis", New Engl. J. Med., 322;1189–1194 (1990).

Li et al., "Apoptosis in an Interleukin–2–Dependent Cytotoxic T Lymphocyte Cell Line is Associated with Intracellular Acidification", J. Biol. Chem., 270:3203–3211 (1995).

Leiberman et al., "Measurement of Sputum Viscosity in a Cone–Plate Viscometer, I. Characteristics of Sputum Viscosity", Am. Rev. Respir. Dis., 97:654–661 (1968).

Leiberman et al., "Measurement of Sputum Viscosity in a Cone–Plate Viscometer, II. An Evaluation of Mucolytic Agents In Vitro", Am. Rev. Respir. Dis., 97:662–672 (1968).

Perez–Sala et al., "Intracellular Alkalinization Suppresses Lovastatin–Induced Apoptosis in HL–60 Cells Through the Inactivation of a pH–Dependent Endonuclease", J. Biol. Chem., 270:6235–6242 (1995).

Wyllie et al., "Cell Death: The Significance of Apoptosis", Int. Rev. Cytol., 68:251–306 (1980).

Morén, F. (1993). Aerosols in Medicine, 2nd edition. Elsevier, Netherlands, pp. 321–350.

Köhler, D. (1993). Aerosols in Medicine, 2nd edition. Elsevier, Netherlands, pp. 303–319.

*Primary Examiner*—Raj Bawa
*Attorney, Agent, or Firm*—Thomas Fitting; Emily Holmes

[57] ABSTRACT

The present invention relates to therapeutic methods for treating diseases characterized by an accumulation of high molecular weight DNA in mucous, thereby contributing to the viscosity of the mucous. Such diseases include cystic fibrosis and chronic bronchitis. Treatment includes administration of weak organic acids to promote acidification of cells and consequently apoptosis-induced DNA fragmentation. The invention also relates to therapeutic apparatus for administering the acid compositions.

18 Claims, 3 Drawing Sheets

TREATMENT OF VISCOUS MUCOUS-ASSOCIATED DISEASES

STATEMENT OF GOVERNMENT SUPPORT

This invention was made with the support of the United States Government, and the United States Government may have certain rights in the invention pursuant to the National Institutes of Health Grant Number AI-24227-10.

TECHNICAL FIELD

The present invention relates to therapeutic methods for treating diseases characterized by an accumulation of DNA in mucous thereby creating viscous mucous. More particularly, the invention relates to the treatment of viscous mucous-associated diseases such as cystic fibrosis (CF) and chronic bronchitis (CB). The therapeutic methods are directed to decreasing the amount of high molecular weight DNA that contributes to the mucous viscosity. Acidifying compositions including weak organic acids and other chemicals are used to promote acidification in DNA-generating cells thereby inducing fragmentation of DNA. The invention also relates to therapeutic apparatus for delivery of the therapeutic composition formulations.

BACKGROUND

In healthy individuals whose lungs are uninfected, lung secretions are complex non-homogeneous materials that form a viscous hydrophilic whitish gel. Mucous glycoproteins in the uninfected lung secretions contribute to the viscosity. However, in infected or purulent yellowish or greenish lung secretions as seen in cystic fibrosis, chronic bronchitis and pneumonia, both mucous glycoproteins and DNA are responsible for increasing the viscosity of the secretions. Cystic fibrosis patients who do not have concurrent bacterial or viral infections also exhibit increased mucous viscosity.

Investigators have determined that DNA, absent from healthy lung secretions, is present in large amounts from 3–14 milligrams/milliliters in purulent lung secretions. See, Chernick et al., *Pediatrics,* 24:739–745 (1959) and Potter et al., *Am. J. Dis. Child,* 100:493–495 (1960). While the viscosity of uninfected as well as infected mucous secretions in individuals with cystic fibrosis, chronic bronchitis or pneumonia was originally thought to be the result of a network of entangled glycoproteins, more recent data suggests that DNA present in the secretions contributes to the entanglement of the network. See, Shak et al., *Proc. Natl. Acad. Sci.*, USA, 87:9188–9192 (1990). Moreover, addition of DNA to a sputum sample has been shown to increase the viscosity of DNA as described by Picot et al., *Thorax,* 33:235–242 (1978).

Further confirmation that DNA contributes to the high viscosity of mucous in various patient populations is based on the reduction of viscosity of lung secretions incubated in vitro with a DNA-specific degrading enzyme, partially purified bovine pancreatic DNase I. See, Armstrong et al., *Lancet*, ii:739–740 (1950) and Chernick et al., *Pediatrics,* 27:589–596 (1961). More recently, recombinant human DNase I has been used in vitro transforming a sample of nonflowing viscous sputum samples from individuals with cystic fibrosis to a flowing liquid. See, Shak et al., *Proc. Natl. Acad. Sci.*, USA, 87:9188–9192 (1990). Aerosolized recombinant human DNase I has now been used as a short-term therapeutic treatment for individuals with cystic fibrosis and chronic bronchitis with similar efficacy to the in vitro results. See. Hubbard et al., *New Engl. J. Med.,* 326:812–815 (1992); Aitken et al., *JAMA,* 267:1947–1951 (1992); and Ranasinha et al., *Lancet,* 342:199–202 (1993).

That enzymatic fragmentation of DNA significantly decreases the viscosity of the mucus suggests that it is not only the amount of DNA present, but its length, which contributes to the viscosity. The origin of the accumulated DNA is attributed to degenerating leukocytes, but little evidence to support this has been published. An alternative source of the DNA is by continuing renewing respiratory epithelial cells that die by programmed cell death and slough into the airway lumen. These cells may well be the source of the excessive DNA present in the mucous secretions of the airway.

The accumulation and persistence of high viscosity secretions contribute to respiratory distress and progressive lung destruction. Specifically, in diseases such as cystic fibrosis, airway secretions are a primary factor in respiratory dysfunction and ultimately contribute to the death of individuals with the disease. The secretions have been characterized as thick and highly viscous. As such, they are difficult to expectorate and contribute to reduced lung volumes and expiratory flow rates. See, for example, Welsh et al., *J. Clin. Invest.,* 80:1523–1526 (1987). In addition, cystic fibrosis patients, as well as persons with chronic bronchitis or pneumonia, are further characterized as having chronic infections of *Pseudomonas aeruginosa* where despite antibiotic therapy, efficacy of treatment with aminoglycoside antibiotics is reduced. See, Potter et al., *Pediatrics,* 36:714–720 (1965), Vandaux et al., *J. Infect. Dis.,* 142:586–593 (1980); and Mendelman et al., *Am. Rev. Respir. Dis.,* 132:761–765 (1985).

The accumulation of viscous secretions in persons with cystic fibrosis is not confined to the respiratory tract, with the intestine, pancreas, biliary tract, salivary glands and genitourinary tract being similarly effected. This multisystem disorder is an autosomal recessive genetic disease due to mutation of the cystic fibrosis transmembrane conductance regulator (CFTR) on the long arm of chromosome 7. The gene occupies 250 kilobases with 27 exons, and encodes a single polypeptide of 1480 amino acids which is N-glycosylated. The CFTR is predominantly expressed in epithelial cells but mRNA can also be detected at much lower levels in leukocytes, skeletal muscle, as well as fetal liver, kidney, heart, and brain. See, Hubbard et al., *New Eng. J. Med.,* 326:812–815 (1992).

The CFTR is a transmembrane anion channel for both chloride and bicarbonate ions that opens in response to cAMP, but has also been shown to regulate chloride conductance through other channels. See, Riordan et al., *Science,* 245:1066 (1989). Over 200 specific mutations of the CFTR gene have been reported, most of which result in the phenotype of cystic fibrosis (CF) in the homozygous state and are asymptomatic when heterozygous. The most common mutation is a three base pair deletion at position 508 (delF508).

In airways of cystic fibrosis individuals, the mutation results in the dysfunction of the CFTR ion channel so that secretion of both bicarbonate and chloride ions are markedly reduced. This inability of epithelia to respond with chloride secretion results in the above-described sequelae. The cellular consequence of the retention of chloride and bicarbonate in the epithelial cells is alkalinization of the cytosol and defective acidification of organelles such as the endoplasmic reticulum, where pH-dependent glycosylation is altered. See, Barash et al., *Nature,* 352:70–73 (1991) and Elgavish et al., *Am. J. Physiol.*, 263:176–186 (1992). Thus, the epithelial cells have a baseline pH that is higher than in comparable normal cells.

Intracellular acidification has been correlated with endonuclease activation in a cell line designated HL-60, a promyelocytic leukemia line, following exposure and damage by the calcium ionophore ionomycin as described by Barry et al., *Biochem. Biophys. Res. Commun.,* 186:782–789 (1992). More recently, the same authors have observed digestion of DNA in HL-60 cells in vitro following exposure to etoposide, an inhibitor of topoisomerase II (Barry et al., *Cancer Res.,* 53:2349–2357 (1993). Within 3.5 hours after exposure to etoposide, the cells underwent concentration-dependent intracellular acidification where the intracellular pH reached maximal acidification of 0.15 pH units. As a result, in a portion of the treated cell population, DNA was shown to be digested through activation of DNase II that requires an acidic environment for activation. Acidification of the cells correlated with the time course of appearance of DNA digestion. The authors suggested that intracellular pH homeostasis may play a role in digestion of genomic DNA that is characteristic of a pathway of cell death referred to as apoptosis or programmed cell death. Investigators using other in vitro systems have also correlated acidification with DNA degradation. See, Caceres-Cortes et al., *J. Biol. Chem.,* 269:12084–12091 (1994) and Li et al., *J. Biol. Chem.*, 270:3203–3211 (1995).

In a recent paper, an inhibitor of protein isoprenylation, lovastatin, was shown to induce DNA degradation in HL-60 cells by first causing a dose-dependent decrease in pH. See, Perez-Sala et al., *J. Biol. Chem.*, 270:6235–6242 (1995). This biological response was observed in a subset of cells whole pH was 0.9 pH units below control levels. In contrast, activation of the sodium/hydrogen antiporter pump resulted in an increase in pH which was sufficient to prevent or arrest DNA degradation. However, the authors stated that lovastatin-induced intracellular acidification was not due to the complete inhibition of the pump. Thus, other biological mechanisms are probably functioning simultaneously in HL-60 cells to promote DNA degradation.

Control of intracellular pH is accomplished through a variety of ion channels and pumps, including the sodium/hydrogen exchanger, the vacuolar proton ATPase, and CFTR in selected cell populations. In one intracellular pH-effecting therapeutic regimen with cystic fibrosis patients having a mutant CFTR, treatment with aerosolized amiloride, an inhibitor of the sodium/hydrogen exchange pump, resulted in an decrease of sputum viscosity with a concomitant improvement in elasticity. See, Knowles, et al., *New Eng. J. Med.,* 322:1189–1194 (1990).

Exposure of a sarcoma cell line to weak acids was shown to result in intracellular acidification only if the extracellular pH was kept at pH 6.5 or less but not if cells were maintained at physiological pH. See Karuri et al., *Brit. J. Cancer,* 68:1080–1087 (1993). With low extracellular pH, the cells were not viable. This effect was probably due to the property that at extracellular physiological pH, the cells' ion-compensating mechanisms were active, while at a lower pH, the cells failed to compensate. Moreover, the authors did not see any acidification in tumors in vivo following intraperitoneal injection of a solution of the weak acids.

Despite the observations described above, the cellular mechanism or mechanisms responsible for the secretion of undegraded genomic DNA found in the sputum of cystic fibrosis patients and the presence of a mutated CFTR protein was equivocal. As a result, the pathophysiological connection between abnormal chloride secretion and the clinical manifestations of cystic fibrosis were previously unclear.

The methods of the present invention are based on the discovery that the cytoplasmic alkalinization caused by the mutant CFTR interferes with the process of DNA fragmentation that depends upon acidification. The methods rely on the findings that acidification is not only a concomitant of or correlated with, but an absolute prerequisite for degradation of DNA ultimately leading to cell death. In addition, an in vitro model system of the present invention has confirmed the direct relationship between acidification and DNA degradation. As such, the failure to degrade DNA in an intracellular alkaline environment contributes to the pathogenesis of cystic fibrosis as senescent CFTR-mutant epithelial cells and/or leukocytes lyse and release undegraded, viscous DNA into the airway lumen.

Fragmentation of DNA has been characterized as one step in a process of programmed cell death, also referred to as apoptosis. Apoptosis was first described by Wyllie et al., *Int. Rev. Cytol.,* 68:251–306 (1980) and is now recognized to be a tightly-regulated physiological process. Although the specific signals regulating apoptosis are poorly understood, cell death by apoptosis is characterized by preservation of the cell membrane (preventing spillage of pro-inflammatory cell contents), crosslinking of cellular proteins by a transglutaminase to form a cornified envelope, DNA fragmentation, condensation and fragmentation of the nucleus into small apoptotic bodies, and expression of markers targeting the cells/apoptotic bodies for phagocytosis (phosphatidylserine, ICAMs). This process is quite efficient, as exemplified by the clearance of enormous numbers of inflammatory cells during the resolution of streptococcal pneumonia.

However, in cystic fibrosis, chronic bronchitis and pneumonia, these processes break down resulting in the clinical profiles described above. While the symptoms of cystic fibrosis can be attributed to the mutant CFTR protein causing an increase in intracellular pH, the accumulation of viscous DNA in individuals suffering from chronic bronchitis and pneumonia is probably due to chronic metabolic alkalosis which results in an increase in intracellular pH, thereby inhibiting the DNA degradation pathway that is facilitated by an acidic intracellular environment. Therefore, in these patients, senescent cells will not undergo apoptosis-induced DNA fragmentation but rather will lyse releasing the high molecular weight DNA into the lumen of the airways.

The novel methods of this invention for ameliorating viscous mucous-associated diseases including cystic fibrosis, chronic bronchitis and pneumonia are based on an in vitro model cell culture system. The model system comprises epithelial cells transfected with the normal and mutant CFTR gene, the latter of which is referred to as delF508. Treatment with exogenously applied acidifying agents have now been discovered to convert a mutant CFTR-transfected cell line, maintained at physiological pH in which apoptosis-induced DNA fragmentation is inhibited, to a cell that exhibits a decrease in intracellular pH resulting in DNA fragmentation.

Thus, the methods of this invention provide a new therapeutic regimen for individuals having a viscous mucous-associated disease by inducing DNA fragmentation and consequently programmed cell death in cells that would have previously undergone lysis without concomitant DNA degradation.

BRIEF SUMMARY OF THE INVENTION

It has been discovered that the deleterious symptoms associated with the accumulation of viscous mucous can be ameliorated by the administration of acidifying agents to the mucous found in the respiratory airways of patients having a viscous mucous-associated disease. The acidification promotes the activity of nucleolytic enzymes which in turn degrades the high molecular weight nucleic acids which cause the mucous to be viscous.

Thus, the invention describes a method for ameliorating viscous mucous-associated disease in a patient with viscous mucous in a respiratory airway of the patient comprising administering a physiologically tolerable composition containing a viscosity-reducing amount of an acidifying agent to the respiratory airway. The disease can be cystic fibrosis, chronic bronchitis, pneumonia and the like viscous mucous-associated disease.

An acidifying agent can be an organic acid, such as propionic, butyric, succinic, malonic, lactic, pyruvic or acetic acid, and can be a pharmacological agent which reduces cellular pH, such as a carbonic anhydrase inhibitor or protein isoprenylation inhibitor.

Effective amounts of a therapeutic composition are typically amounts which reduce the viscosity of the mucous in a patient, and can be monitored by a variety of methods to determine effectiveness. Typically, one can detect reductions in viscosity directly by measurement on a viscometer. Alternatively, one can measure effectiveness indirectly by measuring a 30% or greater increase in sialylation of the glycoproteins in said mucous, indicative of acidification. In addition, one can measure a decrease of the amount of high molecular weight chromatin present in the mucous.

The therapeutic composition can be administered to the respiratory airways in the form of an aerosol using a nebulizer, a small particle aerosol generator or an inhaler with propellants. Alternatively, one can instill a therapeutic composition by lavage.

Also described is an apparatus for delivering therapeutic composition to a patient with a viscous mucous-associated disease comprising:

a) a therapeutic composition containing an acidifying agent;

b) a means for containing the therapeutic composition; and c) a means for delivering the therapeutic composition to respiratory airways of the patient in the form of an aerosol.

The apparatus can include a nebulizer, a small particle aerosol generator or an inhaler with propellant as the means to deliver the therapeutic composition.

BRIEF DESCRIPTION OF THE DRAWINGS

FIG. 2A demonstrates acidification of wild-type CFTR cells treated with CHX (compared to control cells). FIG. 2B demonstrates no change in pH in mutant CFTR cells treated with CHX.

DETAILED DESCRIPTION OF THE INVENTION

Figure 1:
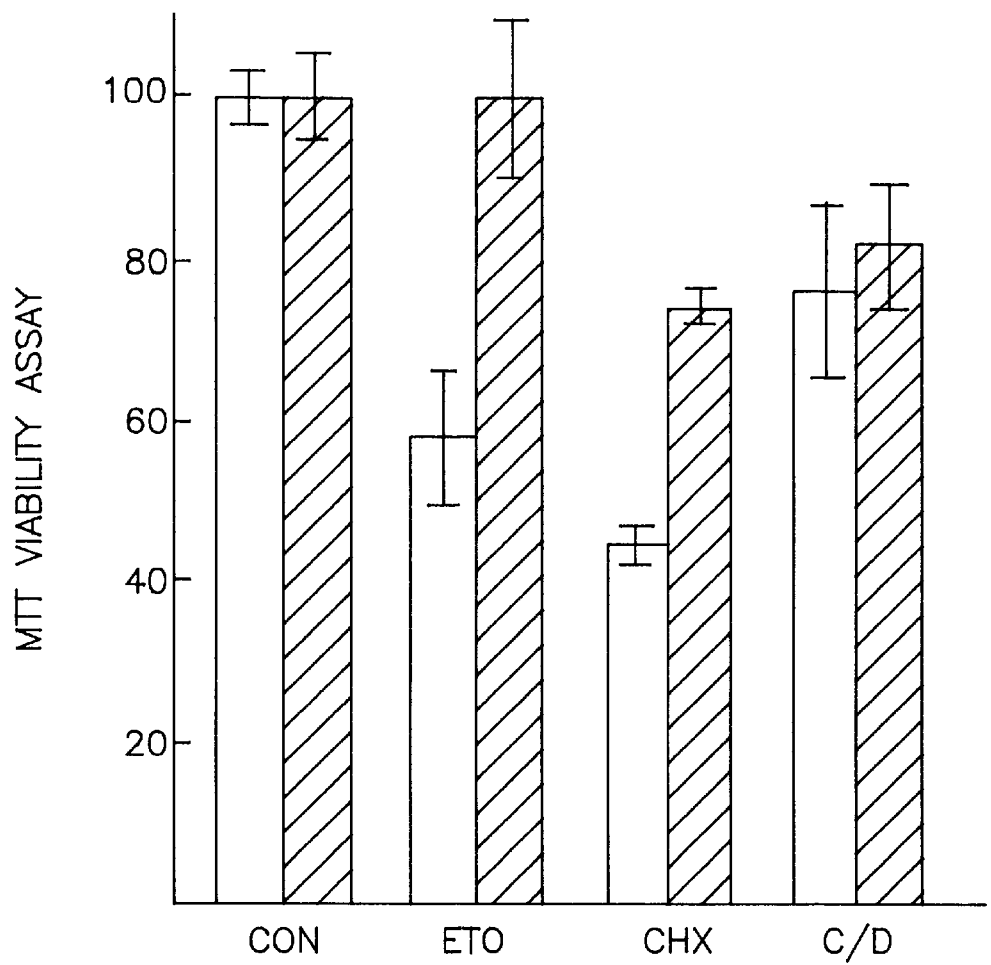
FIG. 1 illustrates the viability of wild type and mutant CFTR-expressing C127 cells 24 hours after exposure to cycloheximide or etoposide. C127 cells expressing the wild type CFTR (clear bars) or the delF508 CFTR (hatched bars) were plated in 96 well plates and treated with 100 μg/ml cycloheximide (CHX), 160 μg/ml etoposide (ETO), or 1 mM diphenylamine carboxylate plus CHX (C/D) for 24 hours, then assayed for MTT reduction as described in Example 2b. Viability is expressed as percent of control activity.

The invention describes methods and apparatus used in the treatment of viscous mucous-associated diseases. The invention depends on the basic discovery that acidification of the tissues of respiratory airways of a patient with such a disease promotes nucleolytic activity in the mucous and in the cells of the tissue, thereby promoting degradation of high molecular weight nucleic acids, which contribute to the viscosity of mucous produced in the tissues of respiratory airways.

A. Therapeutic Methods

Thus, the invention describes a method reducing the undesirable symptoms and effects of accumulated viscous mucous in the respiratory airways of patients with a variety of conditions in which viscous mucous accumulates in the tissues of the airways. By reducing the amount of viscous mucous in the respiratory airways, the viscous mucous-associated disease is ameliorated.

The method comprises administering a physiologically tolerable composition containing a viscosity-reducing amount of an acidifying agent to a respiratory airway of the patient, thereby acidifying the associated tissue and facilitating nucleolytic degradation of accumulated nucleic acids that contribute to the viscosity of the mucous.

1. Viscous Mucous Associated Diseases

The present methods can be practiced on a variety of patients in which there is an undesirable accumulation of mucous in some or all of the respiratory airways as a result of a medical condition. The invention is not to be so limited to any particular disease so long as the amount and viscosity of the mucous has risen to a degree that there are undesirable symptoms in the patient.

Exemplary diseases where mucous accumulates and is viscous producing undesirable symptoms includes cystic fibrosis, chronic bronchitis, pneumonia and the like.

The respiratory airways affected are any in which viscous mucous accumulates. By “viscous mucous” is meant any mucous that accumulates on the apical surface of the respiratory airways in an amount or of a character that renders the accumulation of mucous excessively viscous and thereby deleterious to health. In healthy patients, mucous is removed systematically, but in various diseases, the mucous accumulates excessively and is of a character where the nucleic acid present in the mucous is of high molecular weight and therefor contributes viscosity typical of solutions having high molecular weight DNA. Mucous accumulating in disease conditions also typically has a different constituency in color, cell content, and the like, as is well known, although these differences are not to be considered essential or necessarily limiting to the invention so long as the mucous present is excessive, deleterious and viscous. Under these circumstances, the mucous cannot be readily cleared by the body, and the accumulation contributes to impaired lung function and failure of lung tissues.

The respiratory airways comprise a large and complex collection of organs, that encompasses all of the tissues having surfaces exposed to the passage of air during normal breathing through either the nose or mouth. Thus, the respiratory airways include air-exposed surfaces of the nasal passage, larynx, mouth, trachea, lung bronchi, lung bronchioles, lung alveolar ducts, lung alveolar sacs and lung alveoli, although the lung and associated organs are the primary target for accumulation of viscous mucous.

Thus, the therapeutic composition containing an acidifying agent according to the present invention can be administered to any or all of the affected tissues of the respiratory airways, although the typical and primarily affected airway by accumulation of viscous mucous is the lung, and the associated ducts, sacs and alveoli.

2. Therapeutic Compositions

A therapeutic composition for use in the methods and apparatus of the present invention are physiologically tolerable and contain a therapeutically effective amount of an acidifying agent.

An acidifying agent is any chemical composition, regardless of size, biological activity, mode of action, etc., which, upon contacting the mucous of the respiratory airways, effects a reduction in the viscosity of the mucous by reducing the pH in the mucous, in the cells present in the mucous and in the cells which produce the mucous.

As demonstrated by the present Examples, it is seen that viscous mucous typically has increased pH and an accumulation in the content of high molecular weight nucleic acids. In conditions of high pH, the activity of endogenous nucleolytic enzymes is not at an optimum, and therefore, the cells secreting the mucous and present in the mucous accumulates high molecular weight nucleic acids, thereby contributing to the viscosity of the mucous.

Thus, an acidifying agent can be any reagent which can reduce the pH of the viscous mucous and of the cells in the mucous, and of the cells in the respiratory airways producing the mucous. Typically, the pH should be reduced to from about 5.5 to 6.8 pH units, which pH range is sufficient to support the enzyme activity of nucleolytic enzymes present in the mucous and cells that degrade the high molecular weight nucleic acids and reduce viscosity.

An acidifying agent can typically be of two types. A first type comprises organic acids which act directly by reducing the pH chemically. A second type are pharmacological agents which perturb cellular function to promote acid production in the cells or mucous such that the pH is reduced.

Exemplary organic acids are selected from the group consisting of propionic, butyric, succinic, malonic, lactic, pyruvic and acetic acid. Exemplary pharmacological agents block intracellular acid production. A preferred acidifying agent of this type is a carbonic anhydrase inhibitor or a protein isoprenylation inhibitor. An exemplary carbonic anhydrase inhibitor is acetazolamide. An exemplary protein isoprenylation inhibitor is lovastatin.

Organic acids are available from a variety of commercial sources such as Sigma Chemical Corp, (St. Louis, Mo.). An organic acid can be used in a variety of dosage formulations, but typically are present in a therapeutic composition of from about 0.1 millimolar (mM) to about 1 molar (M). Typically, an organic acid is present in the composition at a neutral or weakly acidic pH, such as from about 5 to 7.4.

Acetazolamide is commercially available as Diamox (Lederle Laboratories, Wayne, N.J.), and is typically present in the composition at a concentration of from about 10 micromolar (uM) to 10 mM, and preferably about 0.1 to 1.0 mm.

Lovastatin is commercially available from Merck Sharpe & Dohme (Westpoint, Pa.), and is typically present in the composition at a concentration of from about 10 micromolar ($\mu$M) to 10 mM, and preferably about 0.1 to 1.0 mM.

Therapeutic compositions of the present invention typically contain a physiologically tolerable carrier together with at least one species of acidifying agent as described herein, dissolved or dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset, toxicity and the like.

The preparation of a pharmacological composition that contains active ingredients dissolved or dispersed therein is well understood in the art. Typically such compositions are prepared as sterile formulations either as liquid solutions or suspensions, aqueous or nonaqueous, however, solid forms suitable for solution, or suspensions, in liquid prior to use can also be prepared. The preparation can also be emulsified. Thus, an acidifying agent-containing composition can take the form of solutions, suspensions, aerosols, or other compositional forms.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol, and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

3. Therapeutically Effective Amounts

The dosage ranges for the administration of an acidifying agent of the invention are those large enough to produce the desired effect in which the disease symptoms mediated by the presence of viscous mucous are ameliorated. An effective amount is an amount which reduces the viscosity of the mucous, i.e., a viscosity reducing amount.

The dosage should not be so large as to cause adverse side effects. Generally, the dosage will vary with the age, condition, sex and extent of the disease in the patient and can be determined by one of skill in the art. The dosage can be adjusted by the individual physician in the event of any complication.

In particular, a therapeutically effective amount is a viscosity-reducing amount of the acidifying agent. A viscosity-reducing amount can be determined in a variety of ways. For example, application of an acidifying agent to a patient having viscous mucous reduces the viscosity if any of a variety of measurable changes are observed in the patient or in the patient's mucous.

For assessing the effectiveness of the therapeutic compositions described above on the amelioration of viscous mucous-associated disease in a patient, such as an individual with cystic fibrosis or chronic bronchitis, direct and indirect assay methods are available.

A direct assay method is one that measures a change in viscosity of a sputum or mucous sample from a patient. One such preferred direct assay is the pourability assay performed as described by Keal, *Postgrad. Med. J.,* 47:171–177 (1971), the disclosure of which is hereby incorporated by reference. In the pourability assay, sputum samples, taken from a patient before and after therapeutic treatment with an acidifying agent of this invention, are aliquoted into 200 to 400 microgram samples. Pourability is qualitatively assessed by inverting the tubes and comparing the movement of sputum after a tap on the side of the tube. The assessment is categorized according to various percentages of movement, such as where 0 equals no movement, 1 equals movement of 10–20% of the sputum, 2 equals movement of 20–50% of the sputum, and the like.

In another preferred direct assay method, viscosity of a sputum sample is measured quantitatively at room temperature using a viscometer, such as a Brookfield cone-plate viscometer. See, Lieberman et al., *Am. Rev. Respir. Dis.,* 97:652–661 and 662–672 (1968), the disclosures of which are hereby incorporated by reference. For viscometer measurements in centipoises, a consistent timed protocol of increased and decreased revolutions per minute of the cone is used.

Other direct assays similar to those described above are familiar to one of ordinary skill in the art of assessing mucous viscosity.

Indirect assays for measuring viscosity are those that are based on either analyses of DNA content and/or quality, on physiological measurements of lung capacity of the patient, on the change in sialylation of glycoproteins in the sputum samples, on the analysis of bacterial content and on the qualitative aspects of well-being as noted by the patient and/or the clinician. In addition, other indirect assays that provide indicia of a change of viscosity of mucous without direct measurement thereof are contemplated for use in determining the efficacy of therapeutic treatment in a patient, such as chest physiotherapy.

For assessing DNA content and/or quality, sputum samples are collected before and after treatment according to the methods of this invention. The collected samples are either directly electrophoresed in an agarose gel or are first subjected to proteolytic degradation by incubation with a solution of proteolytic agents, such as sodium dodecyl sulfate and proteinase K, in the presence of EDTA. Following extraction of the digested sample with phenol/chloroform, the samples are subjected to electrophoresis as described above.

An effect on viscosity is thus indirectly assessed by detecting an alteration of the amount of high molecular weight DNA in the gel. For example, effectiveness of an acidifying agent is indicated if the pretreatment sample contains an electrophoresed band at a particular molecular weight and has a particular width and intensity while the posttreatment sample exhibits a diminished width and intensity at the same molecular weight, assuming that the total sample volume applied is the same.

In parallel, not only is the content of high molecular weight undegraded DNA in the sample reduced with acidifying treatment, but the DNA is degraded into smaller fragments of 300 kilobases or less. Assuming the treated cells proceed to degrade DNA with concomitant lysis of the cells, the smaller molecular weight DNA will be visible on the gels indicating effectiveness of the therapeutic treatment in acidifying DNA-producing cells to facilitate DNA fragmentation. The amount of the degraded DNA will however be dependent on the treated cells' ability to undergo cellular involution rather than lysis.

Another preferred indirect assay for measuring changes in mucous viscosity are physiologic pulmonary tests of lung capacity. Specifically, measurements of forced expiratory volume and forced vital capacity are taken before and after treatment with acidifying agents. The pulmonary lung function test parameters and methods are well known to one of ordinary skill in the art of physiologic lung measurements.

In addition to direct pulmonary measurements, dyspnea, or the shortness of breath, can also be visually assessed and scaled before and after treatment by either the clinician or the patient. The bottom of the scale represents no shortness of breath while the top represents severe shortness of breath. These results can be correlated with visual results of chest X-rays in which degrees of congestion and of degrees of open airways can be detected.

Another preferred indirect assay method is based on the detection of sialylated glycoproteins in the sputum sample after treatment. Cystic fibrosis patients are characterized as having reduced sialylation with N-acetylneuraminic acid (sialic acid) of glycoproteins contained within the mucous. Changes of sialylation can be measured by reacting a sputum sample, either in solution or as immobilized, with a sialic acid binding lectin, such as wheat germ agglutinin, where the latter is labeled with a detectable label such as biotin or a radioactive label. Depending on the label used the sample can be directly read or may require subsequent immunoreaction such as with biotin reacting with avidin labeled with detectable reagent such as horseradish peroxidase. The amount of labeled sample is compared between the untreated and posttreated samples to assess an alteration of sialylation and thereby the effectiveness at acidifying alkalinized cells. Other sialic acid-binding lectins can also be used in this assay as well as others known to those of ordinary skill in the art of glycoprotein biochemistry.

Thus, a preferred method for determining a viscosity reducing amount of a therapeutic composition comprises measuring the amount of sialic acid on the mucous glycoproteins before and after a treatment, wherein an effective amount would be the amount sufficient to induce a 30% or greater increase in the amount of sialylation in the mucous glycoproteins. Methods for determining sialic acids in glycoproteins are well known and not considered to be limiting.

One consequence of patients with cystic fibrosis or chronic bronchitis is persistent bacterial infections that are a consequence of increased viscosity of the secreted mucous. Therefore, another indirect assay to determine the efficacy of therapeutic treatment is to measure the amount bacterial content by standard microbiological techniques in sputum samples before and after acidifying treatment.

Lastly, another preferred method for assessing treatment efficacy is by a quality of life determination based on aspects of well-being including feeling, energy, physical activity, appetite, sleep patterns, and on aspects of disease symptoms including ease of sputum expectoration, cough frequency, cough severity and congestion. The qualities are ranked on a five-point Likert scale in which 1 represents the worst symptoms and 5 represents no symptoms.

The above assays can be used individually or combined in various modalities to provide for an accurate assessment of treatment efficacy in decreasing viscous mucous in a patient.

4. Route of Administration

A therapeutic composition containing an acidifying agent of this invention is conventionally administered by contacting the composition with the mucous or mucous-producing cells in the respiratory airways.

The administration of therapeutic compositions to the respiratory airways is a well developed art in the field, and such methods are applicable here. Typically, an aerosolized or nebulized (vaporous) liquid composition containing a therapeutically-effective amount of an acidifying agent is delivered to the respiratory airways by breathing in the vaporous composition, or by forced (pressurized) periodic inflation breathing of the lungs with the vapor.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the manner of administration. Suitable regimes for administration are also variable, but are typified by an initial administration followed by repeated doses at one or more hour intervals. Alternatively, continuous delivery of an aerosolized or nebulized composition during continuous breathing sufficient to bathe the respiratory airways are contemplated.

Thus, the administration of the vaporous composition can be in the form of a single unit dose, multiple inhalations, or during continuous breathing. Alternatively, a lavage of the lungs may be utilized whereby the lavage solution contains the acidifying agent.

The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

Means for delivering a therapeutic composition comprises a device which produces an aerosol of a liquid composition, which devices are generally well known in the art. These devices can be nebulizers, small particle aerosol generators, inhalers with a propellant, and the like devices.

An exemplary nebulizer includes an Acorn II jet nebulizer, a Marquest or DeVilbiss 646 nebulizer, a compressed air generator such ac a Pulmaide, a Devilbiss, or an IPPB device, which typically nebulize 3–10 milliliters (mL) of solution over about 5–20 minutes, and the like commercially available nebulizers. Aerosol droplets produced by nebulizers are typically of a size that deposits the aerosolized droplets in the larger bronchioles of the lung.

Alternatively, a small particle aerosol generator, such as the commercially available SPAG-2 or Viratek, generates smaller droplets which are deposited more distally in the airways, such as in the ducts and sacs.

The duration and frequency of the administration of a therapeutic composition can vary widely depending upon the severity of the symptoms and infectious state. Typical dosages can be from one unit dose up to a continuous contacting dose over a period of from one to several days. Thus, the contacting can follow a variety of regimens. Exemplary regimens include one or more brief, unit dose, administrations over time to continuously inhaled aerosols for prolonged periods of from 5 minutes up to several hours or even days. More frequent administrations may be used under conditions of rapid cell turnover, such as during infection.

B. Therapeutic Apparatus

The administration of the therapeutic methods can be conducted using an apparatus designed for delivering a therapeutic composition to the respiratory airways of a patient in the form of an aerosol. The apparatus comprises:

a) a therapeutic composition containing an acidifying agent as described herein;

b) a means for containing said therapeutic composition; and c) a means for delivering said therapeutic composition to respiratory airways of said patient in the form of an aerosol.

A means for delivering a therapeutic composition in the form of an aerosol can be any of a variety of devices which generate a liquid droplet-containing vapor as further described herein, and need not be limiting. These devices include a nebulizer, a small droplet aerosol generator, and the like.

The means for containing a therapeutic composition can be any container means which holds the composition as a sterile liquid and presents the liquid for aerosolization and delivery by the delivery means. The container can be made of a variety of materials known in the art.

Other permutations will be apparent to one skilled in the art.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Acidification and DNA Cleavage - Relationship to Apoptosis

Several investigators have shown that acidification accompanies apoptosis. See, Barry et al., *Cancer Res.,* 53:2349–2357 (1993); Caceres-Cortes et al., *J. Biol. Chem.,* 269:12084–12091 (1994); Li et al., *J. Biol. Chem.,* 270:3203–3211 (1995); and Perez-Sala et al., *J. Biol. Chem.,* 270:6235–6242 (1995). The Barry et al. reference describes the induction of apoptosis in human HL-60 cells with a 30 minute exposure with the topoisomerase II inhibitor etoposide. The authors observed that acidification of up to 1 pH unit occurred in about 15% of the cells exposed to etoposide. This change in pH was correlated with the time course of appearance of DNA digestion.

As now determined for use in the methods of this invention, acidification not only occurs in apoptosis but is a prerequisite for apoptosis to proceed. As shown below, acidification precedes DNA cleavage, without which the DNA accumulates intact without the normal apoptotic process of fragmentation, packaging into apoptotic bodies and phagocytosis. As has also been recently determined, DNA cleavage in apoptosis is catalyzed by an acidic endonuclease that requires an acidic environment (pH 6.0) for enzymatic activity.

When cultured in the absence of G-CSF (granulocyte colony-stimulating factor), cultured neutrophils underwent apoptosis and acidified to below pH 6.5. This acidification began early; after 3 hours in culture without G-CSF, a subpopulation of acidified cells was detected. G-CSF protected the neutrophils against apoptosis reducing the number of apoptotic neutrophils to 20% at 20 hours but it also delayed acidification. The basis for the delay in acidification was disclosed by treating the neutrophils with bafilomycin, a powerful and specific inhibitor of vacuolar $H^+$-ATPases.

Bafilomycin had no effect on the G-CSF induced upregulation of a receptor, CD11b, on the neutrophil surface, indicating that it did not interfere with signal transduction by the G-CSF receptor. Bafilomycin did, however, abrogate the protective effect of G-CSF on cultured neutrophils. These results show that G-CSF-mediated upregulation of the neutrophil vacuolar $H^+$-ATPase was responsible for both the delay in acidification and the protection against apoptosis conferred by G-CSF on cultured neutrophils.

Acidification has also been shown to be critical for apoptosis in several other cell types, including CEM and Jurkat thymocyte lines, and the C127 mammary epithelial line. In Jurkat cells, exposure to anti-Fas IgM or to cycloheximide resulted in rapid acidification. Both exposure to various buffering agents and stable transfection with BCL-2 (a gene encoding a protein referred to as B-cell lymphoma 2) prevented acidification and apoptosis as assessed by nuclear morphology and DNA content. Thus, acidification has been determined to be an early and essential event in programmed cell death, without which high molecular weight DNA accumulates in the cell resulting in cellular disruption and release of DNA.

2. Effect of Mutant CFTR on Acidification and Apoptosis

As discussed above, acidification precedes DNA cleavage and is also tightly regulated by multiple signal transduction pathways. Control of intracellular pH is accomplished through a variety of ion channels and pumps, including the sodium/hydrogen exchanger, the vacuolar proton ATPase, and in epithelial cells, the cystic fibrosis transmembrane regulator (CFTR).

The CFTR is a transmembrane anion channel that opens in response to cAMP. Under physiologic conditions, the direction of flow for chloride and bicarbonate is out of the cell as shown by Poulsen et al., *Proc. Natl. Acad. Sci., USA,* 91:5340–5344 (1994). It has been shown that cells expressing the mutant form of the CFTR have a baseline pH that is higher than the comparable normal cells, and fail to acidify cytoplasmic organelles. See, Barasch et al., *Nature,* 352:70–73 (1991) and Elgavish et al., *Am. J. Physiol.,* 263:176–186 (1992).

The most common mutation in CF is deletion of phenylalanine (F) at amino acid residue position 508. Thus, the resulting mutant CFTR is designated as delF508. See, Karem et al., *Science,* 1073–1080 (1989). As cited by Denning et al., *Nature,* 358:761–764 (1992), studies on the biosynthesis and localization of this mutant indicate that the protein is not processed correctly and is not delivered to the plasma membrane. Denning et al. also showed that the mutant is temperature-sensitive reverting to the wild-type when the temperature is reduced.

The therapeutic methods of this invention are based on the determination that the cytoplasmic alkalinization caused by the mutant CFTR interferes with the process of apoptosis that depends upon acidification for DNA fragmentation. That acidification in cells having a mutant CFTR results in an inhibition of apoptosis was determined in a model in vitro cell culture system, using epithelial cells transfected with the normal and a mutant CFTR gene designated delF508, as described in the Examples.

The results of the in vitro cell culture system, as discussed herein, are extrapolatable to the therapeutic methods of this invention for treating DNA-mediated viscosity of mucous. In particular, since the failure to degrade DNA contributes to the pathogenesis of CF and CB when senescent epithelial cells and leukocytes lyse and release undegraded, viscous DNA into the airway lumen, the promotion of acidification in those cells with treatment with acidifying agents including weak organic acids results in activation of an acidic endonuclease that then facilitates the apoptotic-induced DNA fragmentation thereby alleviating the viscosity of the secreted mucous.

a. Preparation of Mouse Epithelial C127 Cell Lines Stably Transfected with Wild-Type CFTR or Mutant CFTR The mouse mammary C127 epithelial cell line was selected as an appropriate cell line for a cell culture system as it does not express the CFTR. Therefore, both the genes encoding the wild-type and a mutated version of the CFTR can be transfected into the recipient cells without any possibility of confounding assay results.

Consequently, the C127 cell line was separately stably transfected with wild-type human CFTR or with mutant CFTR designated as delF508. The cells were transfected as previously described by Denning et al., *Nature,* 358:761–764 (1992). Briefly, the wild-type and mutant transfected cell lines were generated by calcium phosphate-mediated transfection with a bovine papilloma virus-based vector containing CFTR cDNA or the mutant cDNA under control of the mouse metallothionein MT1 promoter and a neomycin-resistance gene as a selectable marker under the control of another copy of the MT1 promoter.

The resulting C127 sublines expressed the wild-type human CFTR or the delF508 mutation. For maintaining the cell sublines, the cells were grown in DMEM with 10% fetal calf serum and 2 mM 1-glutamine, and passaged by trypsinization twice weekly.

b. Apoptosis Assays

1) Exposure to Cycloheximide or Etoposide - Effect on Viability

Mouse mammary C127 cells stably transfected with the wild type or delF508 (mutant) CFTR were plated (5,000 cells/well in 96-well plates) in 96-well plates and allowed to adhere for 1 hour. The attached cells were then incubated in triplicate wells with 100 μg/ml cycloheximide (CHX) in water, 160 μg/ml etoposide (ETO) in 0.1% dimethylsulfoxide (DMSO), or 1 mM diphenylamine carboxylate (DPC) plus CHX (C/D) for 24 hours.

Viability was assessed by reduction of MTT (3-(4,5-dimethylthiazol-2-yl)-2,5-diphenyl tetrazolium bromide). MTT, prepared in a 5 mg/ml solution in PBS, was added to each well (10 μl per 100 μl well) and the cells were incubated for an additional 4 hours. The assay was terminated by the addition of 20% sodium dodecyl sulfate in dimethylformamide. The plates were then read in an ELISA plate reader at 550 nm. The use of this assay for cell viability is well established as described by Mosmann et al., *J. Immun. Meth.,* 65:55–63 (1983).

The results are shown in FIG. 1 where C127 cells expressing the wild type CFTR are represented by clear bars and cells with the delF508 CFTR are represented by hatched bars. Viability is expressed as percent of control activity (cells treated with vehicle alone: water for CHX and 0.1% DMSO for ETO).

As shown in FIG. 1, cells expressing the mutant CFTR were more resistant to the induction of apoptosis by cycloheximide or etoposide than cells expressing the wild-type CFTR. Inhibition of chloride channel function with the inhibitor diphenylamine carboxylate (DPC) converted the wild-type CFTR cell line to a more resistant phenotype, again directly implicating chloride channel activity in the process leading to cell death.

2) Exposure to Cycloheximide or Etoposide - Effect on Nuclear Morphology

To demonstrate that the cell death observed in the wild-type CFTR cells was due to apoptosis, the nuclear morphology was observed in the transfected C127 cells treated as described above.

Cultured wild-type and mutant CFTR C127 cells were separately plated in Chamber Slides (Nunc) and treated with drugs overnight as indicated. The following day, the slides were rinsed with PBS, then fixed for 5 minutes with 4% buffered formaldehyde and rinsed with methanol before air drying. Nuclear morphology was assessed after staining with a 4 82 g/ml solution of acridine orange as described in Morphological and Biochemical Assays of Apoptosis; in: *Current Protocols in Immunology,* 3.17.1 (1992). Cells were then photographed at 400× magnification on a fluorescence microscope.

The results of the above assay and staining revealed that the characteristic nuclear condensation observed in apoptosis was present with a high frequency in wild-type CFTR cells treated with cycloheximide, but only rarely in the mutant counterparts. Treatment with etoposide yielded similar results.

3) Exposure to Cycloheximide - Effect on DNA Degradation

The ability of CFTR-transfected C127 cells to degrade their DNA upon exposure to cycloheximide was then assessed. For this assay, the wild-type and mutant CFTR transfected cells were plated in Chamber Slides (Nunc) as described above and then treated as previously described with cycloheximide overnight. The treated cells were then in situ nick end labeled by a modification of the method of Wijsman et al., *J. Histochem. Cytochem.,* 41:7–12 (1993), in which cells were fixed for 5 minutes with 4% formaldehyde in PBS and rinsed with methanol.

For the labeling, each treated cell sample was then incubated with a reaction mixture containing 0.05 μM biotin-14-dATP, and 5 μM each dTTP, dCTP, and dGTP, in 50 mM Tris-HCl (pH 7.5), 5 mM $MgCl_2$, 0.1 mg/ml BSA, and 10 U/ml Klenow fragment, for 30 minutes at room temperature. Slides were rinsed with PBS, incubated with 0.28% periodic acid, rinsed, incubated with PBS containing 2% BSA for 5 minutes, then incubated with streptavidin-peroxidase (1:1000) (Kirkegaard and Perry Labs) for 30 minutes and rinsed twice with PBS. Color was developed with Enhance Black according to the manufacturer's instructions (Kirkegaard and Perry Labs).

The labeling study showed that nuclei with DNA fragmentation were strongly labeled by this method. CHX treatment induced the fragmentation of DNA in the wild-type CFTR cells but not in the mutant counterparts.

4) Endonuclease Activity of C127 Nuclear Extracts

Since DNA degradation was dependent upon acidification and activity of an acid endonuclease, it was important to determine if the C127 cell line possessed acid endonuclease activity. Nuclear extracts therefore were prepared and endonuclease activity was measured under a variety of pH and ionic conditions.

For preparation of nuclear extracts, epithelial cell lines were washed in PBS, then lysed in 10 mM Tris-HCl, pH 7.5, 1.5 mM $MgCl_2$, 0.5% NP-40 for 15 minutes on ice. The nuclear pellet obtained after sedimentation (2000×g) was resuspended in 3 volumes of nuclear extract buffer (20 mM Tris-HCl at pH 7.5, 0.4M NaCl, 1.5 mM $MgCl_2$, 1 mM DTT, and 25% glycerol) and incubated for 30 minutes at 4° C. with gentle shaking. After sedimentation at 17,000×g, the supernatant (nuclear extract) was stored at −70° C. until use.

For performing a plasmid DNA digestion assay, 1 μl of nuclear extract was incubated at 37° C. for 1 hour with 100 ng supercoiled plasmid DNA in APT buffer (10 mM sodium acetate, 10 mM potassium phosphate, 10 mM Tris-HCl) at pH 5.5 or cation buffer (30 mM Tris-HCl, pH 7.4, with 5 mM $CaCl_2$, 5 mM $MgCl_2$ as indicated) in a volume of 50 μl. At the end of the 1 hour reaction, SDS (0.2%) and EDTA (10 mM) were added, followed by glycerol sample buffer. Samples were resolved electrophoretically on a 1% agarose gel containing 0.5 μg/ml ethidium bromide.

Various reaction conditions were evaluated including the following: the reaction mixture at pH 5.5; the reaction mixture at pH 7.5; the reaction mixture at pH 7.5 with 5 mM Ca++; the reaction mixture at pH 7.5 with 5 mM Mg++; the reaction mixture at pH 7.5 with both Ca++and Mg++. Endonuclease activity was indicated by the conversion of supercoiled plasmid DNA to open circle form, followed by linearization and progressive digestion.

Analysis of the electrophoresed samples showed that the C127 cells contained acid endonuclease activity as well as calcium- and magnesium-dependent endonuclease activity, indicated by degradation of supercoiled DNA to open circle and linear forms as well as degradation to smaller fragments. This suggests that the C127 cells possessed the necessary machinery for DNA cleavage, but were unable to do so when the mutant CFTR was expressed.

5) Exposure to Cycloheximide - Effect on Intracellular pH

To determine if acidification occurred in the C127 transfected cells used in the in vitro model for CF and related diseases, the epithelial cell preparations were treated overnight with DMSO (vehicle control), etoposide (160 μg/ml), or cycloheximide (100 μg/ml), then harvested by trypsinization with EDTA. Cells in suspension were labeled for 30 minutes with 10 μM carboxy-SNARF-1-AM, washed and resuspended in Hanks' Balanced Salt Solution with 0.1 mM EDTA (to prevent aggregation), and analyzed by flow cytometry. A Coulter Elite flow cytometer was used with excitation at 488 nm and emission analysis at 575 and 620 nm. Ten thousand events were collected and data plotted as forward scatter versus fluorescence ratio. Intracellular pH was estimated by comparison to the fluorescence intensity ratio of cells which are pH-adjusted by incubation with nigericin (10 μM) in a high-potassium buffer as described Musgrove et al., *Meth. Cell Biol.,* 33:59–69 (1990).

Figure 2A:
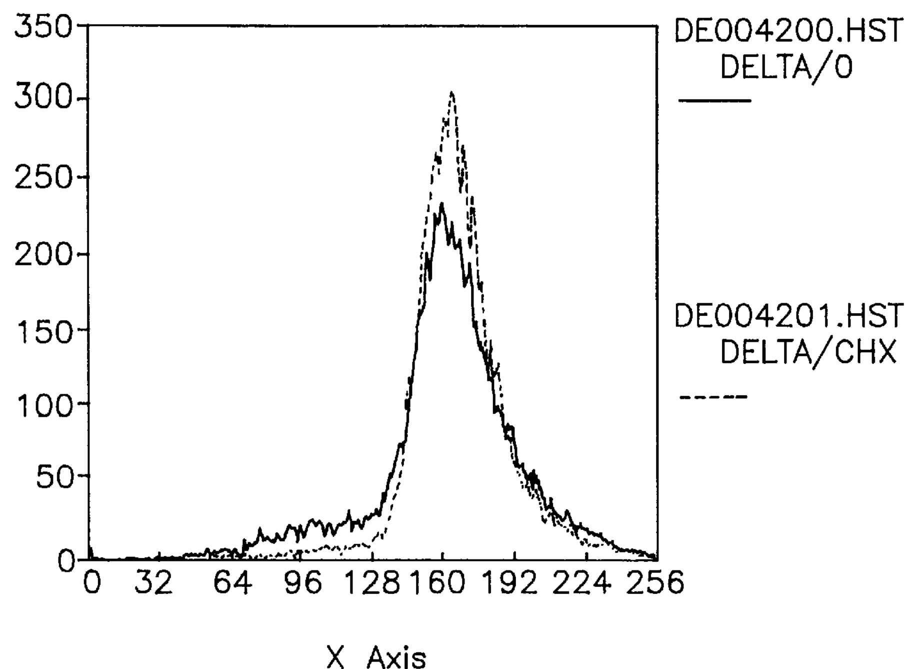
FIGS. 2A and 2B respectively show the flow cytometric analysis of intracellular pH of wild-type CFTR and mutant CFTR cells treated with cycloheximide for 24 hours. Cells were treated with buffer (control, solid line) or with 100 μg/ml cycloheximide (CHX, dashed line) for 24 hours, detached by trypsinization, loaded with carboxy-SNARF-1-AM, and analyzed by dual emission ratio analysis. Vertical axis denotes cell number; horizontal axis denotes fluorescence ratio, with lower pH to the left.
Figure 2B:
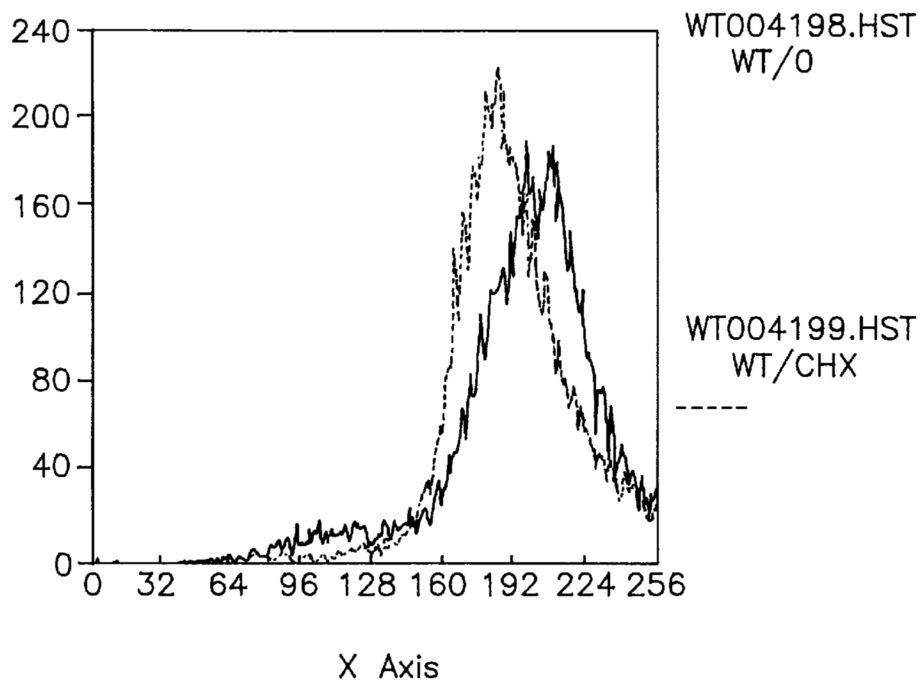

The results of the flow cytometry analysis are shown in FIGS. 2A and 2B. Cells treated with buffer are labeled as control as shown with a solid line. The corresponding CHX-treated cells are shown with a dashed line. Vertical axis denotes cell number; horizontal axis denotes fluorescence ratio, with lower pH to the left. FIG. 2A demonstrates acidification of wild-type CFTR cells treated with CHX (compared to control cells). FIG. 2B demonstrates the effect on pH in mutant CFTR cells treated with CHX.

Cycloheximide induced acidification in the wild-type CFTR cell line but had no effect on intracellular pH in the mutant CFTR cells, consistent with the absence of apoptosis in these cells.

3. Effect of Propionic Acid on Viability of Transfected C127 Cell Lines

To determine if the resistance to apoptosis in the mutant CFTR line could be overcome by promoting acidification, cells were cultured with cycloheximide in the presence or absence of the weak organic acid, propionic acid (10 mM, adjusted to pH 7.4). After overnight culture, cell viability was measured using the MTT assay as described in Example 2*b*.

Figure 3:
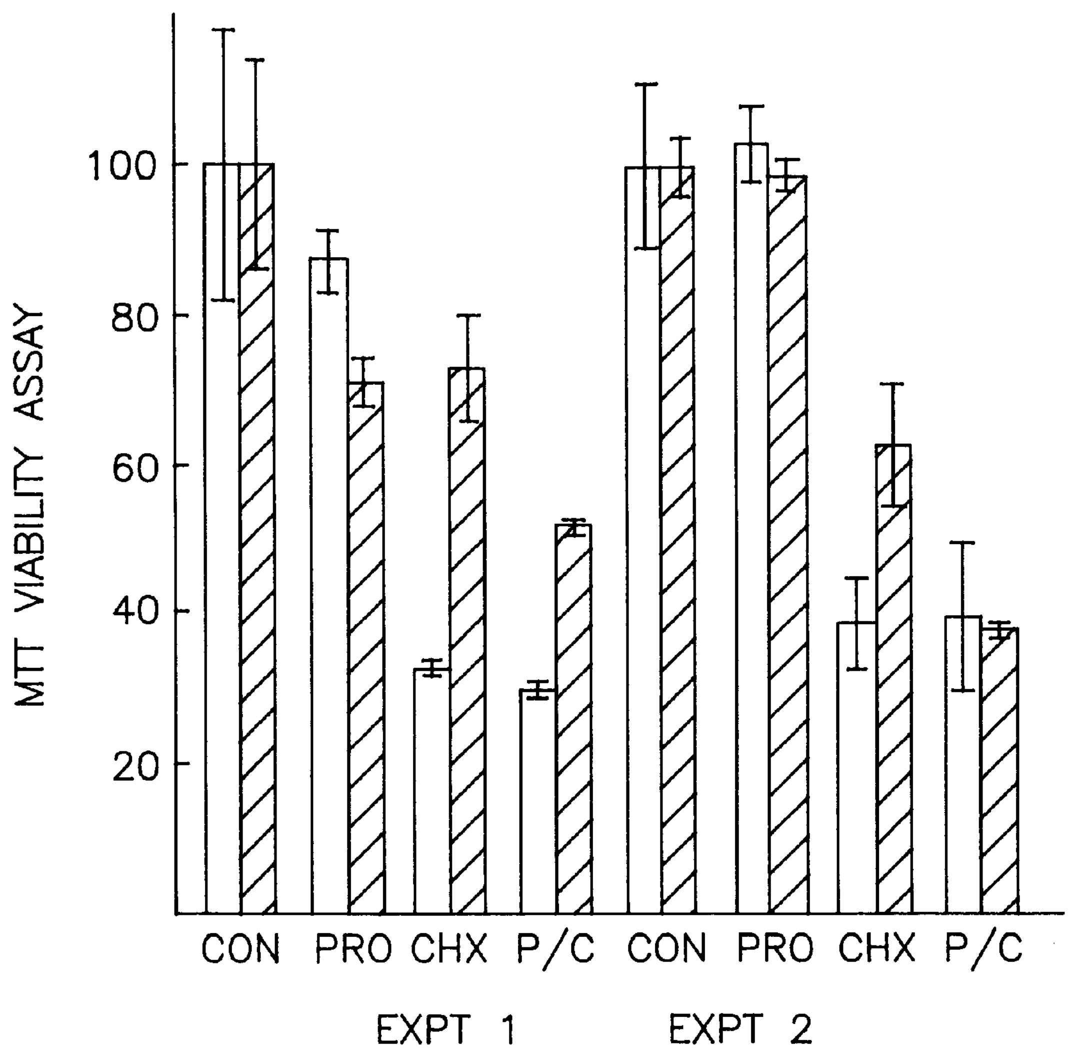
FIG. 3 shows the viability assay of cells treated with cycloheximide plus propionic acid. Wild-type CFTR cells (clear bars) and mutant CFTR cells (hatched bars) were treated as described in FIG. 1 with no additions (control, CON), with propionic acid (10 mM, pH 7.4) (PRO), cycloheximide (100 μg/ml) (CHX), or propionic acid plus CHX (P/C). Results are presented as percent viability relative to the control; error bars indicate standard deviation of triplicate samples. Two experiments are shown.

The results of this assay are shown in FIG. 3. Wild-type and mutant CFTR cells are respectively indicated with clear bars and hatched bars. The cells were separately treated as described for FIG. 1 with no additions (control, CON), with propionic acid (10 mM, pH 7.4) (PRO), cycloheximide (100 μg/ml) (CHX), or propionic acid plus CHX (P/C). Results are presented as percent viability relative to the control; error bars indicate standard deviation of triplicate samples. Two experiments are shown.

As shown in FIG. 3, propionic acid sensitized the mutant CFTR cells to the induction of apoptosis by CHX, but had little or no effect on viability of control cells (mutant or wild type), or of wild-type CFTR cells treated with CHX. These findings indicate that exogenous acidification enables the mutant CFTR cells to undergo apoptosis in response to alteration of the ionic environmental signal.

4. Summary

By several criteria described above, apoptosis or programmed cell death has been shown to occur in epithelial cells transfected with the wild-type but not the mutant CFTR, in response to cycloheximide and etoposide. Markers of cell viability, nuclear morphology, and DNA fragmentation all demonstrated that the wild-type CFTR cells underwent apoptosis while mutant CFTR cells did not. The C127 cell lines possessed the acid endonuclease and other cellular machinery necessary for apoptosis; the only difference was the expression of the mutant CFTR, with its consequent effect to limit the ability of the cell to lower its intracellular pH, which is a necessary event in physiologic cell death.

This invention thus demonstrates the essential role of a functional CFTR in permitting apoptosis and DNA cleavage in epithelial cells. The CFTR secretes chloride and bicarbonate in a cAMP-dependent manner, and may be subject to regulation by other pathways. The consequence of bicarbonate secretion is intracellular acidification, which, if the acidification is profound enough, would be expected to permit DNA fragmentation by the acid endonuclease. The mutant CFTR is unable to secrete bicarbonate in response to cAMP; the consequence is a higher resting pH and an inability to acidify in response to appropriate stimuli. Dysfunction of the CFTR was reproduced by treating the wild-type cells with the chloride channel inhibitor DPC, which had the effect of making the wild-type cells as resistant to the induction of apoptosis as the mutants.

These results are thus consistent with and therefore provide a valid in vitro model for the therapeutic basis of the invention. In particular, the results indicate that therapeutic treatment of patients with alkalinization-induced viscous mucous-associated disease, by administration of an acidifying agent, such as propionic acid as well as those described in the specification, promotes the process of apoptosis, particularly DNA digestion, thereby ameliorating the disease state.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A method for ameliorating viscous; mucous-associated disease selected from the group consisting of cystic fibrosis, chronic bronchitis and pneumonia, in a patient with viscous mucous in a respiratory airway of said patient comprising administering a physiologically tolerable composition containing a viscosity-reducing amount of an acidifying agent, selected from the group consisting of an organic acid and a pharmacological agent that increases intracellular acid production resulting in a pH range of 5.5 to 6.8, to said respiratory airway, wherein said administering is by aerosolized, vaporized, nebulized or lavage delivery.

2. A method for reducing the content of high molecular weight nucleic acid in mucous in a patient with cystic fibrosis comprising administering a mucous-reducing amount of a physiologically tolerable composition containing an acidifying agent, selected from the group consisting of an organic acid and a pharmacological agent that increases intracellular acid production resulting in a pH range of 5.5 to 6.8, to the airways of said patient, wherein said administering is by aerosolized, vaporized, nebulized or lavage delivery.

3. The method of claim 2 wherein said organic acid is selected from the group consisting of propionic, butyric, succinic, malonic, lactic, pyruvic and acetic acid.

4. The method of claim 2 wherein said mucous-reducing amount is an amount sufficient to induce 30% or greater increase in sialylation of the glycoproteins in said mucous.

5. The method of claim 2 wherein said respiratory airway includes one or more of nasal passage, larynx, trachea, lung bronchi, lung bronchioles, lung alveolar ducts, lung alveolar sacs and lung alveoli.

6. The method of claim 1 wherein said organic acid is selected from the group consisting of propionic, butyric, succinic, malonic, lactic, pyruvic and acetic acid.

7. The method of claim 1 wherein said organic acid is present in said composition at a concentration of from 0.1 mM to 1M.

8. The method of claim 6 wherein said composition contains 10 to 50 mM propionic acid in an isotonic, neutral pH, buffered aqueous liquid.

9. The method of claim 1 wherein said pharmacological agent is a carbonic anhydrase inhibitor.

10. The method of claim 9 wherein said carbonic anhydrase inhibitor is acetazolamide.

11. The method of claim 9 wherein said composition contains 10 $\mu$M to 10 mM of said inhibitor.

12. The method of claim 1 wherein said viscosity-reducing amount is an amount sufficient to induce 30% or greater increase in sialylation of the glycoproteins in said mucous.

13. The method of claim 1 wherein said viscosity-reducing amount is an amount sufficient to decrease the amount of high molecular weight chromatin in said mucous by 50% or greater.

14. The method of claim 1 wherein said respiratory airway includes one or more of nasal passage, larynx, trachea, lung bronchi, lung bronchioles, lung alveolar ducts, lung alveolar sacs and lung alveoli.

15. The method of claim 1 wherein said nebulized administering comprises contacting said respiratory airway with said composition using a nebulizer.

16. The method of claim 1 wherein said aerosol administering comprises contacting said respiratory airway with said composition using a small particle aerosol generator.

17. The method of claim 1 wherein said aerosol administering comprises contacting said respiratory airway with said composition using an inhaler with propellant.

18. The method of claim 1 wherein said composition is contacted with said respiratory airway in the form of an liquid aerosol for a time period of 5 minutes to 24 hours.

* * * * *